US008628578B2

(12) United States Patent
Miller et al.

(10) Patent No.: US 8,628,578 B2
(45) Date of Patent: Jan. 14, 2014

(54) EXPANDABLE INTERBODY IMPLANT AND METHODS OF USE

(75) Inventors: Keith E. Miller, Germantown, TN (US); Stanley T. Palmatier, Olive Branch, MS (US); Anthony J Melkent, Memphis, TN (US); William D Armstrong, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 209 days.

(21) Appl. No.: 13/329,802

(22) Filed: Dec. 19, 2011

(65) Prior Publication Data

US 2013/0158663 A1    Jun. 20, 2013

(51) Int. Cl.
*A61F 2/44* (2006.01)

(52) U.S. Cl.
USPC ................................. 623/17.16; 623/17.11

(58) Field of Classification Search
USPC ................................. 623/17.11, 17.15, 17.16
See application file for complete search history.

(56) References Cited

U.S. PATENT DOCUMENTS

| 5,658,336 | A | 8/1997 | Pisharodi |
| 5,665,122 | A | 9/1997 | Kambin |
| 5,980,522 | A | 11/1999 | Koros et al. |
| 6,102,950 | A | 8/2000 | Vaccaro |
| 6,299,642 | B1 | 10/2001 | Chan |
| 6,491,724 | B1 | 12/2002 | Ferree |
| 6,835,206 | B2 | 12/2004 | Jackson |
| 6,955,691 | B2 | 10/2005 | Chae et al. |
| 7,070,598 | B2 | 7/2006 | Lim |
| 7,087,055 | B2 | 8/2006 | Lim |
| 7,118,579 | B2 | 10/2006 | Michelson |
| 7,214,243 | B2 | 5/2007 | Taylor |
| 7,320,555 | B2 | 1/2008 | Chang et al. |
| 7,410,501 | B2 | 8/2008 | Michelson |
| 7,445,636 | B2 | 11/2008 | Michelson |
| 7,621,960 | B2 | 11/2009 | Boyd et al. |
| 7,655,027 | B2 | 2/2010 | Michelson |
| 7,655,046 | B2 | 2/2010 | Dryer |
| 7,753,958 | B2 | 7/2010 | Gordon |
| 7,763,078 | B2 | 7/2010 | Peterman et al. |
| 7,828,849 | B2 | 11/2010 | Lim |
| 7,846,185 | B2 | 12/2010 | Carls et al. |
| 2002/0068976 | A1 | 6/2002 | Jackson |

(Continued)

FOREIGN PATENT DOCUMENTS

WO    WO 2010/147844    * 12/2010

OTHER PUBLICATIONS

International search report for child application, PCT/US12/63208.*

*Primary Examiner* — Kevin T. Truong
*Assistant Examiner* — Christian Sevilla

(57) ABSTRACT

An intervertebral implant comprises a first component and a second component. The second component includes an actuator and a third component comprises a first ramp and a second ramp axially spaced apart from the first ramp. The third component comprises rails including at least a portion of the ramps. At least one of the ramp portions disposed with the first rail has a first height and at least one of the ramp portions disposed with the second rail has a second height. The first height is greater than the second height. The actuator is engageable with the third component to effect axial translation such that the ramps engage at least one of the components between a first configuration and a second configuration. Methods of use are disclosed.

18 Claims, 5 Drawing Sheets

(56) References Cited

U.S. PATENT DOCUMENTS

| Publication No. | Date | Name | Ref |
|---|---|---|---|
| 2002/0068977 A1 | 6/2002 | Jackson | |
| 2004/0010315 A1 | 1/2004 | Song | |
| 2004/0087947 A1 | 5/2004 | Lim | |
| 2004/0249466 A1 | 12/2004 | Liu et al. | |
| 2005/0113916 A1 | 5/2005 | Branch, Jr. | |
| 2005/0113917 A1 | 5/2005 | Chae et al. | |
| 2006/0241643 A1 | 10/2006 | Lim | |
| 2006/0241770 A1 | 10/2006 | Rhoda | |
| 2006/0247778 A1 | 11/2006 | Ferree et al. | |
| 2006/0259147 A1* | 11/2006 | Krishna et al. | 623/17.15 |
| 2008/0058938 A1 | 3/2008 | Mujwid | |
| 2008/0177387 A1* | 7/2008 | Parimore et al. | 623/17.16 |
| 2009/0112319 A1 | 4/2009 | O'Neil | |
| 2009/0171461 A1 | 7/2009 | Conner | |
| 2010/0057208 A1 | 3/2010 | Dryer | |
| 2010/0204795 A1 | 8/2010 | Greenhalgh | |
| 2010/0286780 A1 | 11/2010 | Dryer | |
| 2010/0286783 A1 | 11/2010 | Lechmann | |
| 2010/0292796 A1* | 11/2010 | Greenhalgh et al. | 623/17.11 |
| 2011/0029082 A1 | 2/2011 | Hall | |
| 2011/0054621 A1 | 3/2011 | Lim | |
| 2011/0093074 A1* | 4/2011 | Glerum et al. | 623/17.16 |
| 2011/0172774 A1* | 7/2011 | Varela | 623/17.16 |

\* cited by examiner

EXPANDABLE INTERBODY IMPLANT AND METHODS OF USE

TECHNICAL FIELD

The present disclosure generally relates to medical devices, systems and methods for the treatment of musculoskeletal disorders, and more particularly to an expandable interbody implant system and method for treating a vertebral column.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility. For example, after a disc collapse, severe pain and discomfort can occur due to the pressure exerted on nerves and the spinal column.

Non-surgical treatments, such as medication, rehabilitation and exercise can be effective, however, may fail to relieve the symptoms associated with these disorders. Surgical treatment of these spinal disorders includes fusion, fixation, discectomy, laminectomy and implantable prosthetics. These treatments may employ interbody implants. This disclosure describes an improvement over these prior art technologies.

SUMMARY

Accordingly, an expandable interbody implant system and method are disclosed. In one embodiment, an intervertebral implant is provided. The intervertebral implant comprises a first component comprising an outer tissue engaging surface and an inner surface. A second component is connected to the first component and is relatively moveable therefrom. The second component comprises an outer tissue engaging surface and an inner surface. The second component includes an actuator. A third component is disposed for engagement and is movable relative to the first and second components. The third component comprises a first ramp and a second ramp axially spaced apart from the first ramp. The third component comprises a first rail including at least a portion of each of the first ramp and the second ramp. A second rail includes at least a portion of each of the first ramp and the second ramp. At least one of the ramp portions disposed with the first rail has a first height and at least one of the ramp portions disposed with the second rail has a second height. The first height is greater than the second height. The actuator is engageable with the third component to effect axial translation of the third component such that the ramps engage the inner surface of one of the first component and the second component to move the components between a first, collapsed configuration and a second, expanded configuration.

In one embodiment, the intervertebral implant comprises a piston component comprising an endplate surface and an inner surface disposed in an opposing orientation relative to the endplate surface. The piston component extends between an anterior end and a posterior end. A base component comprises an endplate surface and an inner surface disposed in an opposing orientation relative to the endplate surface of the base component. The base component extends between an anterior end and a posterior end. The base component includes an actuator. A wedge is disposed for engagement and is movable relative to the piston and base components. The wedge comprises a first ramp and a second ramp axially spaced apart from the first ramp, and a third ramp axially spaced apart from the second ramp. The wedge comprises an anterior rail including at least a portion of each of the first ramp, the second ramp and the third ramp, and a posterior rail including at least a portion of each of the first ramp, the second ramp and the third ramp. The actuator is engageable with the wedge to effect axial translation of the wedge such that the ramps engage the inner surface of the piston component to move the components between a first, collapsed configuration and a second, expanded configuration.

In one embodiment, a method for treating a spine is provided. The method comprises the steps of: providing an intervertebral implant comprising: a first component having an anterior end and a posterior end, the first component comprising an outer tissue engaging surface and an inner surface, a second component having an anterior end and a posterior end, the second component comprising an outer tissue engaging surface and an inner surface, the second component including an actuator, and a third component disposed for engagement and being movable relative to the first and second components, the third component comprising a first ramp and a second ramp axially spaced apart from the first ramp, the third component comprising a first rail including at least a portion of each of the first ramp and the second ramp and a second rail including at least a portion of each of the first ramp and the second ramp, at least one of the ramp portions disposed with the first rail has a first height and at least one of the ramp portions disposed with the second rail has a second height, the first height being greater than the second height; introducing the intervertebral implant in a collapsed configuration along a direct lateral approach of a body within an intervertebral space; and engaging the actuator with the third component to effect axial translation of the third component relative to the first and second components such that the ramps engage the inner surface of one of the first component and the second component to expand the intervertebral implant to a second, expanded configuration.

BRIEF DESCRIPTION OF THE DRAWINGS

The present disclosure will become more readily apparent from the specific description accompanied by the following drawings, in which.

DETAILED DESCRIPTION

Figure 1:
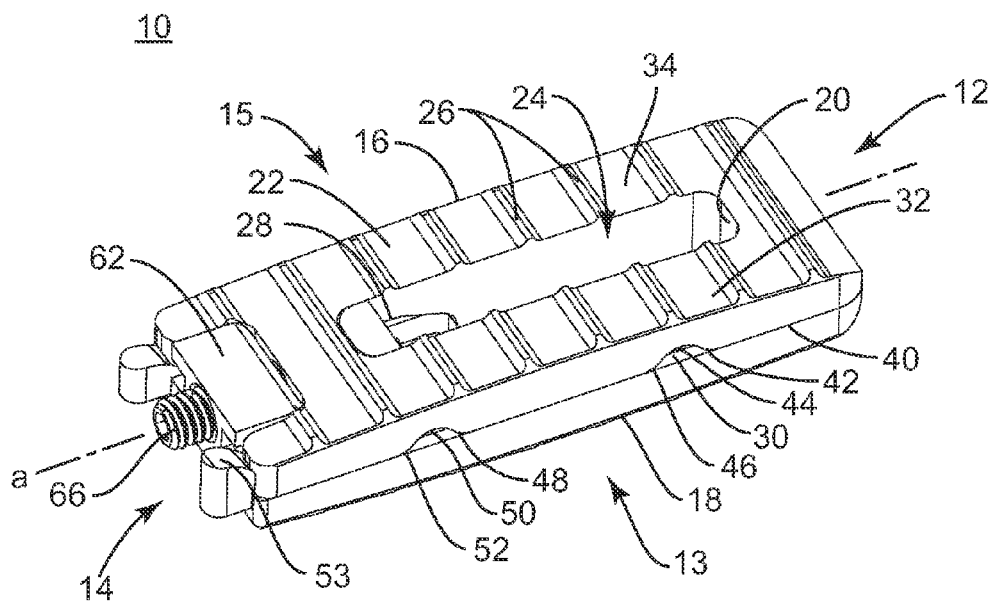
FIG. 1 is a perspective view of one embodiment of an implant of a system in accordance with the principles of the present disclosure.
Figure 2:
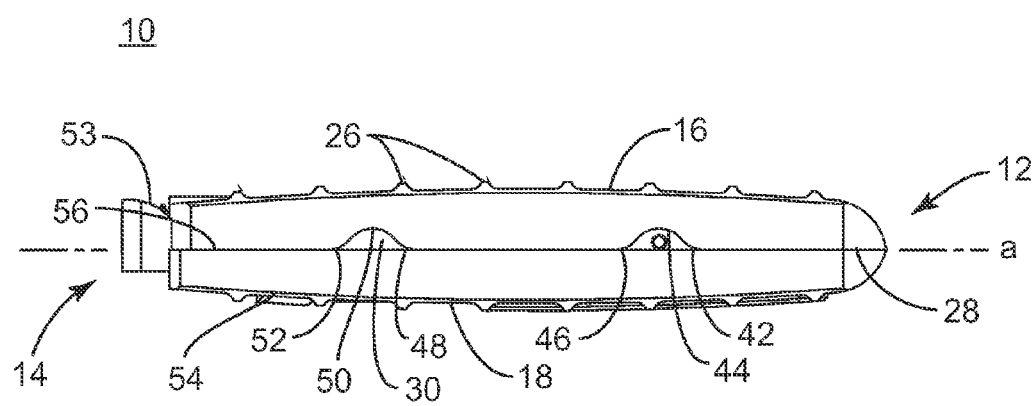
FIG. 2 is a side view of the implant shown in FIG. 1.

The exemplary embodiments of an expandable interbody implant system and related methods of use disclosed herein are discussed in terms of medical devices for the treatment of musculoskeletal disorders and more particularly, in terms of an expandable interbody implant system and related methods for treating a vertebral column. It is envisioned that the implant system may provide, for example, fusion, decompression, restoration of sagittal balance and resistance of subsidence into tissue, such as, for example, surfaces of vertebral endplates. It is further envisioned that the system includes an interbody implant that expands after insertion into an intervertebral disc space and has several features, such as, for example, facile insertion into the intervertebral disc space such that less bone removal is necessary during a surgical procedure, decompression of nerve roots, expansion to restore sagittal balance such that more expansion is provided on an anterior side relative to a posterior side in, for example, a lumbar application.

In one embodiment, the expandable interbody implant system is employed with a direct lateral approach to the intervertebral disc space such that the anterior side of the interbody implant expands more than the posterior side of the interbody implant to restore lordosis. In one embodiment, the expandable interbody implant includes a base component that engages a first vertebral endplate, a piston component that engages a second vertebral endplate disposed in an opposing orientation and a multiple ramp component that is driven between the base and piston components to drive the base and piston components apart. It is contemplated that the multiple ramp component is moved relative to the base component via an actuator component. It is further contemplated that the triple multiple ramp component can include three wedges that drive apart the piston and base components at the proximal and distal ends of the expandable interbody implant. It is envisioned that the height and angle of each wedge selectively provides an amount and rate of expansion on each end of the expandable interbody implant. For example, a steeper and/or taller wedge on a distal and/or anterior portion of the expandable interbody implant drives lordosis as the interbody implant is expanded.

It is envisioned that the expandable interbody implant and methods of use disclosed herein can be employed to obtain fusion of vertebrae through a minimally invasive or percutaneous technique. In one embodiment, the disclosed expandable interbody implant and methods of use can provide restoration of lordosis by expanding the anterior side of the device more than on the posterior side. It is contemplated that the expandable interbody implant and methods of use disclosed herein provide, for example, relatively constant bone graft volume, which maintains the bone graft and vertebral endplate contact.

It is envisioned that the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. It is contemplated that the present disclosure may be employed with other osteal and bone related applications, including those associated with diagnostics and therapeutics. It is further contemplated that the disclosed expandable interbody implant may be alternatively employed in a surgical treatment with a patient in a prone or supine position, and/or employ various surgical approaches to the spine, including anterior, posterior, posterior inidine, medial, lateral, postero-lateral, and/or antero-lateral approaches, and in other body regions. The expandable interbody implant of the present disclosure may also be alternatively employed with procedures for treating the lumbar, cervical, thoracic and pelvic regions of a spinal column. The expandable interbody implant and methods of the present disclosure may also be used on animals, bone models and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, outer, inner, terminal (denoting position or location), left and right, posterior, anterior, and the like, are for illustrative purposes only and can be varied within the scope of the disclosure. For example, the references "superior" and "inferior" are relative and used only in the context to the other, and are not necessarily "upper" and "lower".

Further, as used in the specification and including the appended claims, "treating" or "treatment" of a disease or condition refers to performing a procedure that may include administering one or more drugs to a patient in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (for example, preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, for example, arresting its development, or relieving the disease, for example, causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of an expandable interbody implant and related methods of employing the expandable interbody implant in accordance with the principles of the present disclosure. Alternate embodiments are also disclosed. Reference will now be made in detail to the exemplary embodiments of the present disclosure, which are illustrated in the accompanying figures. Turning now to FIGS. 1-9, there is illustrated components of an interbody implant system including an intervertebral implant 10 in accordance with the principles of the present disclosure.

The components of the system can be fabricated from biologically acceptable materials suitable for medical applications, including metals, synthetic polymers, ceramics and bone material and/or their composites, depending on the particular application and/or preference of a medical practitioner. For example, the components of the system, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (for example, Nitinol, super elasto-plastic metals, such as GUM METAL® manufactured by Toyota Material Incorporated of Japan), ceramics and composites thereof such as calcium phosphate (for example, SKELITE™ manufactured by Biologix Inc.), thermoplastics such as polyaryl ether ketone (PAEK) including polyether ether ketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polylactide, polyglycolide, polytyrosine carbonate, polycaprolactone and their combinations. Various components of the system may be fabricated from material composites, including the above materials, to achieve various desired characteristics such as strength, rigidity, elasticity, flexibility, compliance, biomechanical performance, durability and radiolucency or imaging preference. The components of the system, individually or collectively, may also be fabricated from a heterogeneous material such as a combination of two or more of the above-described materials.

The system including intervertebral implant 10 can be employed as a stabilization device in fusion and fixation procedures, for example, for patients suffering from a spinal disorder to provide height restoration between vertebral bodies, decompression, restoration of sagittal balance and/or resistance of subsidence into vertebral endplates. The components of the interbody implant system may be monolithically formed, integrally connected or include fastening elements and/or instruments, for example, as described herein.

Figure 4:
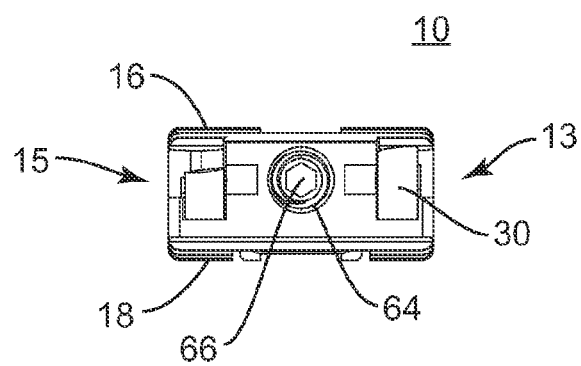
FIG. 4 is a side view of the implant shown in FIG. 1.
Figure 9:
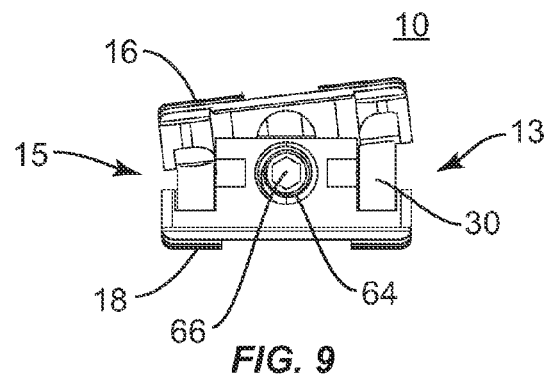
FIG. 9 is a side view of the implant shown in FIG. 1.

Intervertebral implant 10 defines a longitudinal axis a and extends between a first end 12 and a second end 14. Implant 10 also extends between an anterior end 13 and a posterior end 15, as shown in FIGS. 1, 4 and 9. Intervertebral implant 10 includes a first component, such as, for example, a piston component 16 and a second component, such as, for example, a base component 18 connected to piston component 16. Base component 18 is movably mounted to piston component 16 via an actuator, described below. Piston component 16 includes a wall 20 that defines an opening that captures the actuator. This configuration maintains connection of the components of intervertebral implant 10 as an integral or unitary assembly to facilitate a pivoting connection between components 16, 18. Components 16, 18 are relatively movable to expand and collapse with intervertebral implant 10 between a first configuration and a second configuration, as will be described. It is contemplated that components 16, 18 may be monolithically formed and/or be connected via a living hinge. It is further contemplated that base component 18 may be alternatively connected to piston component 16 by integral connection, press fit, threaded, adhesive and/or fastening elements such as clips and/or screws. It is envisioned that intervertebral implant 10 may include one or a plurality of components.

Piston component 16 includes an outer tissue engaging surface, such as, for example, an endplate surface 22. Endplate surface 22 defines a substantially rectangular opening 24 extending therethrough. It is envisioned that opening 24 may be configured for packing of at least one agent, for example, bone graft. It is further envisioned that opening 24 may have alternate configurations, such as, for example, oval, oblong, triangular, square, polygonal, irregular, uniform, non-uniform, offset, staggered, undulating, arcuate, variable and/or tapered. It is contemplated that endplate surface 22 may include one or a plurality of openings.

Endplate surface 22 is configured to engage an endplate of a vertebra and includes a plurality of raised elements 26 configured to enhance fixation and/or gripping with vertebral tissue. Elements 26 are disposed transverse to longitudinal axis a. It is envisioned that all or only a portion of endplate surface 22 may have alternate surface configurations to enhance fixation with tissue such as, for example, rough, arcuate, undulating, mesh, porous, semi-porous, dimpled and/or textured according to the requirements of a particular application. It is further envisioned that elements 26 may be disposed at alternate orientations, relative to axis a, such as, for example, perpendicular and/or other angular orientations such as acute or obtuse, co-axial and/or may be offset or staggered.

Piston component 16 includes an inner surface 28 disposed to face an opposing orientation and/or direction relative to the facing orientation and/or direction of endplate surface 22. Endplate surface 22 is oriented in a direction to face tissue of a vertebral endplate and inner surface 28 is oriented to face an opposite direction. Inner surface 28 is substantially smooth or even and configured to engage a surface of a third component, such as, for example, a wedge 30 such that wedge 30 is movable relative to components 16, 18.

Piston component 16 includes a first extension 32 and a second extension 34 extending in a substantially linear configuration along longitudinal axis a between a first end 12 and a second end 14. Extensions 32, 34 are monolithically formed with first end 12 and second end 114. It is envisioned that extensions 32, 34 may be alternatively connected to ends 12, 14 by integral connection, press fit, threaded, adhesive and/or fastening elements such as hinge, clip and/or screws. Extensions 32, 34 are disposed in a substantially parallel orientation relative to longitudinal axis a. It is contemplated that extensions 32 and/or 34 may be disposed at alternate orientations, relative to longitudinal axis a, for example, perpendicular, converging, diverging and/or other angular orientations such as acute or obtuse, co-axial and/or may be offset or staggered. It is envisioned that extensions 32, 34 may extend in alternate configurations such as, for example, radius of curvature, offset and/or staggered. It is further envisioned that extensions 32, 34 may have various cross section configurations, such as, for example, oval, oblong, triangular, rectangular, square, polygonal, irregular, uniform, non-uniform, variable, hollow and/or tapered.

Each of extensions 32, 34 include at least a portion of inner surface 28 that engages at least a portion of the surface of wedge 30 to expand and collapse intervertebral implant 10 between a first configuration and a second configuration, as will be described. For example, each of extensions 32, 34 include a planar portion 40, a first inclined portion 42, a first recess portion 44, a first transition 46, a second inclined portion 48, a second recess portion 50, a second transition 52 and a third inclined portion 53. Portions 40, 42, 44, 46, 48, 50, 52 and 53 are disposed in series along each of extensions 32, 34. Inclined portions 42, 48 and 53 are disposed at an angle from axis a. It is contemplated that extension 32 and/or extension 34 may include one or a plurality of inclined portions, or one extension may include an inclined portion(s) and the other extension may include no inclined portion.

Base component 18 includes an outer tissue engaging surface, such as, for example, an endplate surface 54. It is envisioned that endplate surface 54 may include one or a plurality of openings configured for packing of at least one agent, for example, bone graft. Endplate surface 54 is configured to engage an endplate of a vertebra and includes raised elements 27 configured to enhance fixation and/or gripping with vertebral tissue. Elements 27 are disposed transverse to longitudinal axis a. It is envisioned that all or only a portion of surface 54 may have alternate surface configurations to enhance fixation with tissue similar to those alternatives described herein. It is further envisioned that elements 27 may be disposed at alternate orientations, relative to longitudinal axis a, similar to those alternatives described herein.

Base component 18 includes an inner surface 56 disposed to face an opposing orientation and/or direction relative to the acing orientation and/or direction of endplate surface 54. Endplate surface 54 is oriented in a direction to face tissue of a vertebral endplate and inner surface 56 is oriented to face an opposite direction. Inner surface 56 is planar and substantially smooth or even and configured to engage a surface of wedge 30. Inner surface 56 engages the surface of wedge 30 such that wedge 30 is movable relative to components 16, 18.

Base component 18 extends in a substantially linear configuration along longitudinal axis a between first end 12 and a second end 14. Base component 18 includes a wall 62 that defines an elongated cavity, such as, for example, threaded opening 64. An actuator, such as, for example, a threaded screw 66 is configured for disposal within threaded opening 64 and extends through the opening of wall 20 to a distal end 68 that is fixed with wedge 30.

Screw 66 is rotatable relative to wall 62 in a first direction, such as clockwise, and a second opposing direction, such as counter clockwise. Screw 66 is configured to mate with threaded opening 64 in a threaded engagement and distal end 68 is fixed with wedge 30 and freely rotatable therein. Screw 66 is caused to engage opening 64 and rotated in a selected direction such that screw 66 is threaded with opening 64. Screw 66 is configured for translation relative to wall 62 in a first axial direction and a second axial direction.

Figure 5:
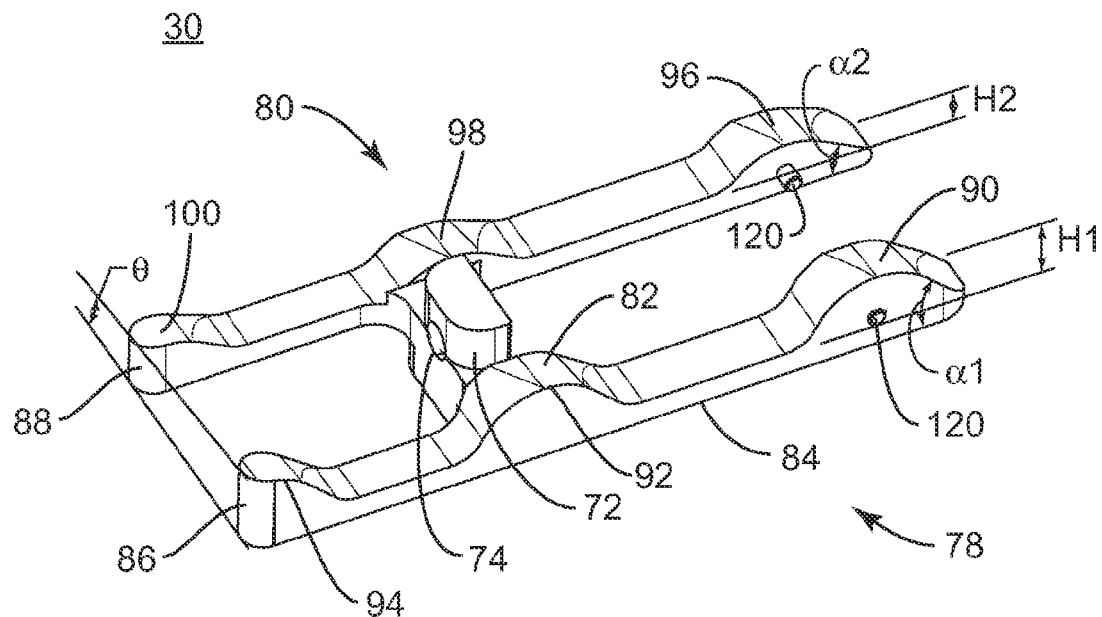
FIG. 5 is a perspective view of a component of the implant shown in FIG. 1.
Figure 6:
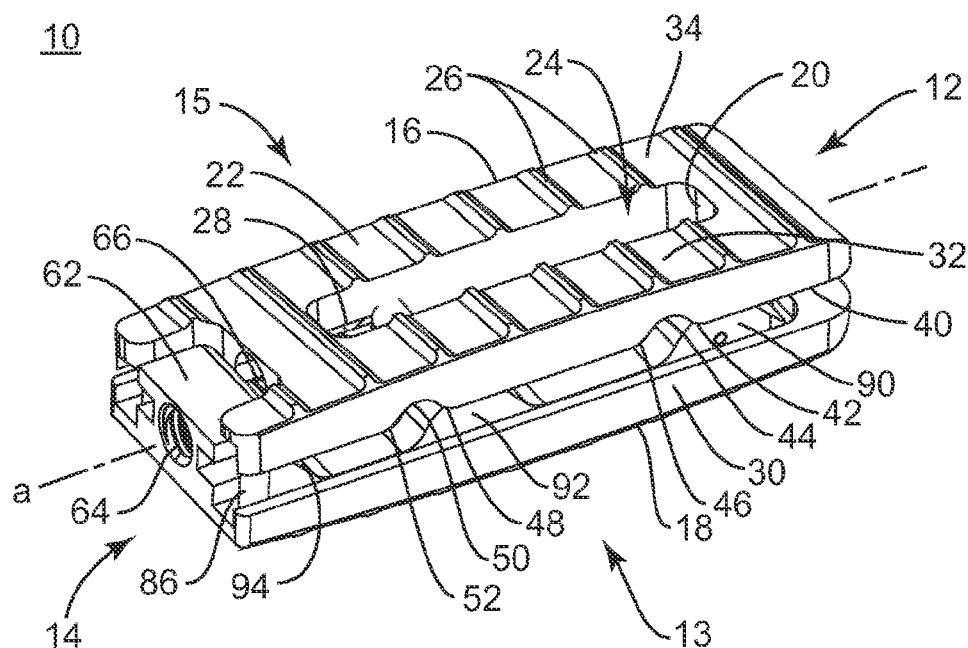
FIG. 6 is a perspective view of the implant shown in FIG. 1.
Figure 7:
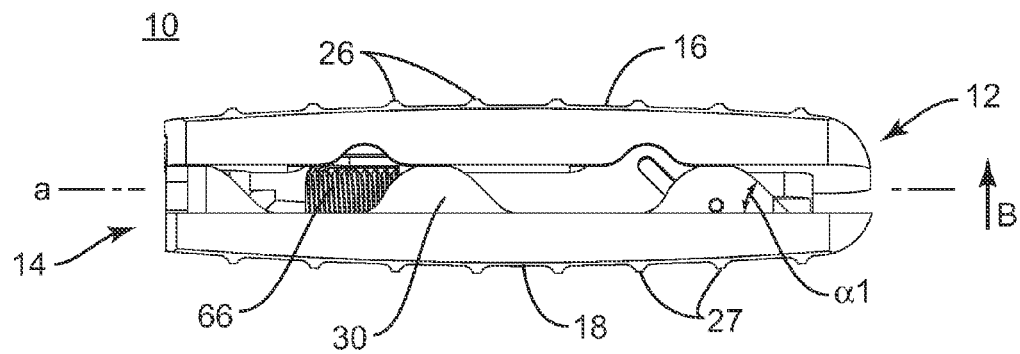
FIG. 7 is a side view of the implant shown in FIG. 1.

Distal end 68 includes a flange 70 that engages a wall 72 of wedge 30 to retain screw 66 with wedge 30, as shown in FIG. 5. Distal end 68 extends through an opening 74 of wall 72 and includes a reduced diameter (not shown) such that distal end 68 rotates relative to wall 72 to facilitate axial translation of screw 66 and wedge 30. The reduced diameter of distal end 68 facilitates engagement of screw 66 with wall 72 to drive and axially translate wedge 30, in a first direction shown by arrow A in FIG. 8. Flange 70 engages wall 72 to draw and axially translate wedge 30, in a second opposing direction shown by arrow C.

Screw 66 is fixed with wedge 30 to effect axial translation of wedge 30 such that wedge 30 is movable relative to components 16, 18 to expand and collapse intervertebral implant 10 between a first configuration and a second configuration, as will be described. Screw 66 is engaged with an instrument or tool (not shown), to facilitate actuation of the component parts of intervertebral implant 10 and disposal thereof in various configurations according to the requirements of a particular application.

Wedge 30 is disposed in an intermediate orientation with components 16, 18. Wedge 30 includes an anterior side 78 and a posterior side 80. Wedge 30 includes a first surface 82 that engages piston component 16 and a second surface 84 that engages base component 18 such that wedge 30 is movable for axial translation relative to components 16, 18. Wedge 30 includes a first rail portion, such as, for example, anterior rail 86 located on anterior side 78 and a second rail portion, such as, for example, posterior rail 88 located on posterior side 80 disposed along longitudinal axis a, which movably engage components 16, 18 to expand and collapse intervertebral implant 10 between a first configuration and a second configuration.

First rail portion 86 on anterior side 78 includes a first ramp, such as, for example, wedge portion 90 and a second ramp, such as, for example, wedge portion 92 and a third ramp, such as, for example, wedge portion 94. Wedge portion 90 is axially spaced apart from wedge portion 92 along rail portion 86. Wedge portion 94 is axially spaced apart from wedge portion 92 along rail portion 86. Wedge portions 90, 92 and 94 on anterior side 78 have a first height H1 (FIG. 5) and a first angle of inclination $\alpha 1$ (FIG. 7) relative to longitudinal axis a. It is envisioned that height H1 may be in a range of 2 millimeters (mm) to 10 mm. It is further envisioned that angle $\alpha 1$ may be in a range of 5 to 60 degrees. It is contemplated that rail portion 86 may include one or a plurality of ramps, or may include no ramp.

Second rail portion 88 on posterior side 80 includes a first ramp, such as, for example, wedge portion 96 and a second ramp, such as, for example, wedge portion 98 and a third ramp, such as, for example, wedge portion 100. Wedge portion 96 is axially spaced apart from wedge portion 98 along rail portion 88. Wedge portion 98 is axially spaced apart from wedge portion 100 along rail portion 88. Wedge portions 96, 98 and 100 on posterior side 80 have a second height H2 and a second angle of inclination $\alpha 2$ relative to axis a. It is envisioned that height H2 may be in a range of 0 mm to 7 mm. It is envisioned that angle $\alpha 2$ may be in a range of 0 to 60 degrees. It is contemplated that angle $\alpha 2$ may be dependent on ramp configuration. It is contemplated that rail portion 88 may include one or a plurality of ramps, or may include no ramp.

In one embodiment, height H1 is greater than height H2. In one embodiment, angle $\alpha 1$ is greater than angle $\alpha 2$. The height differentiation results in a restoration of lordosis as the device is being expanded. First rail portion 86 and second rail portion 88 wedge portions have angle ranges between preferably about 10° to about 45° and most preferably about 20° to about 35°.

First rail portion 86 and second rail portion 88 are connected via wall 72. It is contemplated that wedge portions 90, 92 and 94 on anterior side 78 and wedge portions 96, 98 and 100 on posterior side 80 drive apart components 16, 18 to facilitate expansion and collapse of intervertebral implant 10 between a first configuration and a second configuration. It is further contemplated that the height and/or angle of the anterior side 78 and posterior side 80 regulates the amount and rate of expansion of intervertebral implant 10. It is envisioned that wedge portions 90, 92 and 94 and wedge portions 96, 98 and 100 are monolithically formed, connected by fastening elements or a separate and distinct structure.

Each of rail portions 86, 88 include at least a portion of first surface 82 that engages at least a portion of inner surface 28 of piston component 16 to expand and collapse intervertebral implant 10 between a first configuration and a second configuration. For example, the portions of surface 82 including wedge portions 90, 92 and 94 disposed along rail portion 86 slideably engage portions 40, 42, 44, 46, 48, 50, 52 and 53 disposed along extension 32. The portions of surface 84 including wedge portions 96, 98 and 100 disposed along rail portion 88 slideably engage portions 40, 42, 44, 46, 48, 50, 52 and 53 disposed along extension 34. Each of rail portions 86, 88 also include at least a portion of surface 84 that slideably engages at least a portion of inner surface 56 corresponding to base component 18.

Rail portions 86, 88 extend for disposal about wall 62 adjacent end 14. Rail portions 86, 88 move about wall 62 during axial translation of the component parts of intervertebral implant 10.

Figure 3:
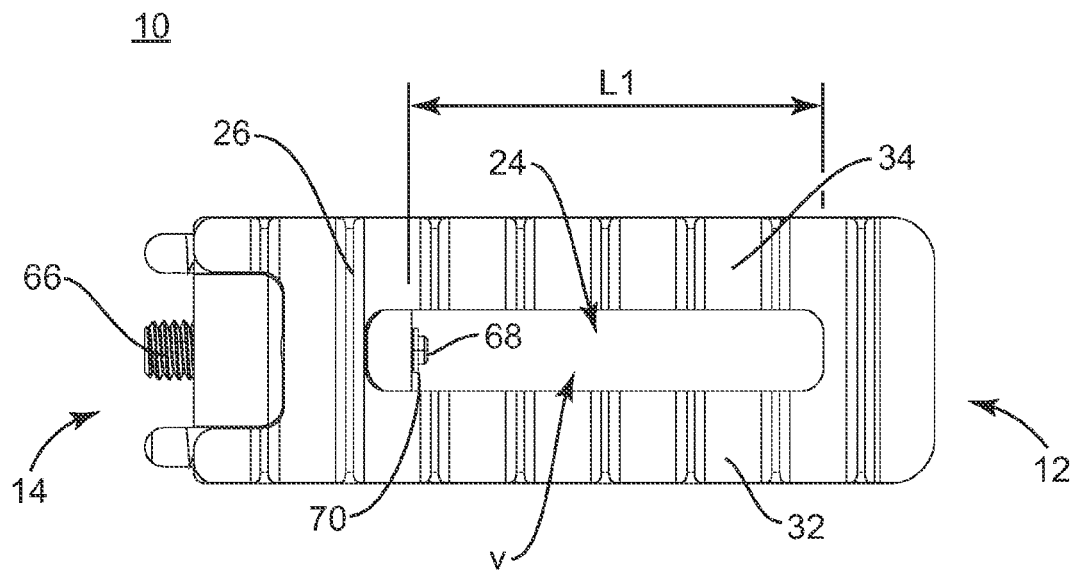
FIG. 3 is a plan view of the implant shown in FIG. 1.
Figure 8:
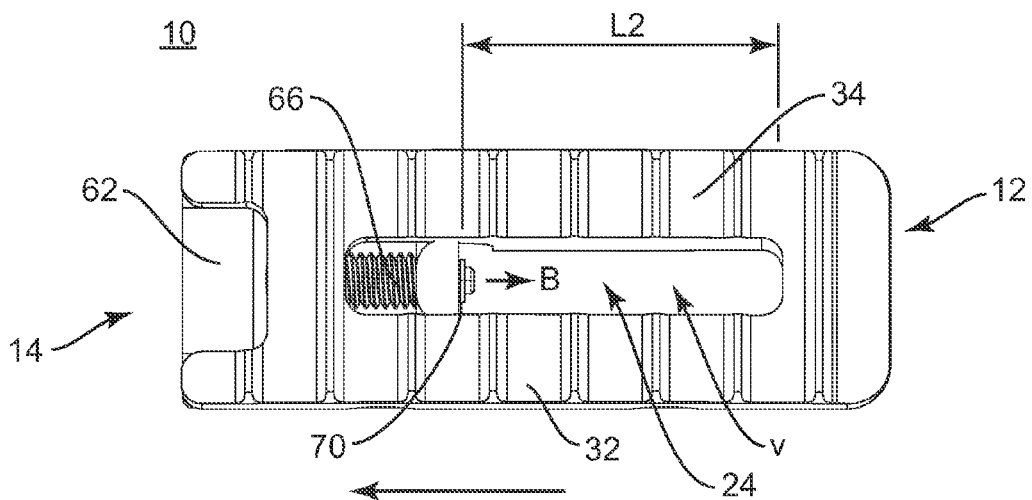
FIG. 8 is a plan view of the implant shown in FIG. 1.

In one embodiment, as shown in FIGS. 3 and 8, intervertebral implant 10 is configured to minimize the volume change of bone graft disposed with implant 10. Opening 24 extending through components 16, 18 and 30. Opening 24 is configured for disposal of at least one agent, for example, bone graft. In the first, collapsed configuration (FIGS. 1-4), opening 24 defines a length L1 (FIG. 3) and cross sectional area such that a volume v of bone graft is disposed within opening 24. Wall 72 of wedge 30 is disposed in a proximal position. As intervertebral implant 10 is expanded to the second, expanded configuration (FIGS. 6-9), the overall height of implant 10 increases and wall 72 is translated axially in the direction shown by arrow A in FIG. 8, as described herein. As wall 72 axially translates, the cross-sectional area of opening 24 is decreased. Wall 72 is translated to a distal position such that opening 24 defines a length L2 (FIG. 8). The decrease in length of opening 24 to length L2 and the increase in overall height of implant 10 maintain volume v of bone graft relatively constant. It is contemplated that this configuration for maintaining bone graft volume avoid the bone graft becoming loose within opening 24 as implant 10 increases in height. It is further contemplated that tightly packed bone graft can potentially increase fusion capability.

In operation, as shown in FIGS. 1-9, intervertebral implant 10 is engaged for disposal between a first configuration and a second configuration such that intervertebral implant 10 expands in an intervertebral disc space. Intervertebral implant 10 is engaged with an instrument (not shown) to facilitate actuation of the component parts of intervertebral implant 10 according to the requirements of a particular surgical application.

In a first configuration, such as, for example, a collapsed configuration (FIGS. 1-4), components 16, 18 are disposed in a low profile orientation with wedge 30 such that planar portions 40 of extensions 32, 34 are disposed adjacent to inner surface 56. Wedge portions 90, 96 are disposed in flush engagement with the respective inclined portions 42 of extensions 32, 34, wedge portions 92, 98 are disposed in engagement with the respective inclined portions 48 of extensions 32, 34 and wedge portions 94, 100 are disposed in engagement with the respective inclined portions 53 of extensions 32, 34.

Upon desired positioning of intervertebral implant 10 according to the requirements of a particular surgical application, screw 66 is manipulated to move wedge 30 axially. The instrument engages screw 66 for rotation in a clockwise direction. Screw 66 translates axially in a first axial direction shown by arrow A. As screw 66 translates axially, distal end 68 engages wall 72 to drive wedge 30 axially. Wedge portions 90, 96 slidably engage the respective inclined portions 42, wedge portions 92, 98 slidably engage the respective inclined portions 48 and wedge portions 94, 100 slidably engage the respective inclined portions 53. Such slidable engagement of the surfaces of wedge 30 and components 16, 18, due to the axial translation of wedge 30, pivots component 16 relative to component 18 in rotation, as shown by arrow B in FIG. 7, such that components 16, 18 expand between the first collapsed configuration and the second, expanded configuration (FIGS. 6-9). This configuration facilitates expansion of intervertebral implant 10 due, at least in part, to first rail portion 86 being a greater height relative to second rail portion 88. It is contemplated that a steeper and/or taller rail portion 86 facilitates lordosis as intervertebral implant 110 is expanded. In one embodiment, components 16, 18 can be expanded to an angle of lordosis L. It is envisioned that angle L may be in a range of approximately 5-30 degrees.

In one embodiment, components 16, 18 can be expanded to create lordosis at an oblique angle. Rail portion 86 and/or rail portion 88 may include a ramp configuration having one or a plurality of ramps that increase in height from end 12 to end 14, or alternatively, from end 14 to end 12. Similar to that described above, the height of the ramps on one rail portion is greater than the height on the other rail portion. This configuration of implant 10 creates a lordosis from a selected corner of the body of implant 10 to an opposing corner of the body of implant 10. It is contemplated that such lordotic configuration extends diagonally across the surfaces of components 16, 18. It is further contemplated that this configuration provides an oblique approach to an intervertebral disc space, for example, between a direct lateral approach and a posterior approach, and/or between a direct lateral approach and an anterior approach.

In one embodiment, intervertebral implant 10 can be collapsed from the expanded configuration to an alternate configuration between the expanded and collapsed configurations, via manipulation of wedge 30 in a second axial direction, as shown by arrow C in FIG. 8, opposite to the first axial direction. It is envisioned that reciprocal axial movement of wedge 30 to collapse intervertebral implant 10 may be desired to reposition or remove intervertebral implant 10 from a body cavity. Upon disposal of intervertebral implant 10 in the expanded configuration, to dispose intervertebral implant 10 in an alternate configuration, screw 66 is rotated in a counterclockwise direction such that distal end 68 engages wall 72 to draw and axially translate wedge 30, in the second opposing direction shown by arrow C.

As wedge 30 is translated axially in the second axial direction, component 16 pivots to rotate toward the collapsed configuration such that wedge portions 90, 96 move toward engagement with the respective inclined portions 42, wedge portions 92, 98 move toward engagement with the respective inclined portions 48 and wedge portions 94, 100 move toward engagement with the respective inclined portions 53. Depending on the application, components 16, 18 may be returned to the fully collapsed configuration, as shown in FIGS. 1-4.

In one embodiment, wedge 30 includes pins 120 disposed on anterior and posterior sides thereof. Pins 120 are disposed with wedge 30 for slidable movement within slots defined within piston component 16. As wedge 30 is translated axially in the second axial direction, component 16 pivots to rotate toward the collapsed configuration such that wedge portions 90, 96 move toward engagement with the respective inclined portions 42, wedge portions 92, 98 move toward engagement with the respective inclined portions 48 and wedge portions 94, 100 move toward engagement with the respective inclined portions 53.

In assembly and use, the interbody implant system is employed with a surgical procedure, such as, a fusion treatment of a spine of a patient including vertebrae V (not shown), intervertebral disc space I (not shown) and body areas adjacent thereto, as discussed herein. The interbody implant system may also be employed with other surgical procedures, such as, for example, discectomy, laminotomy, laminectomy, nerve root retraction, foramenotomy, facetectomy, decompression, and spinal, nucleus or disc replacement.

For example, the interbody implant system can be employed with a surgical arthrodesis procedure, such as, for example, an interbody fusion for treatment of an applicable condition or injury of an affected section of a spinal column and adjacent areas within a body, such as, for example, intervertebral disc space I between first vertebrae V1 (not shown) and second vertebrae V2 (not shown) of vertebrae V. It is contemplated that intervertebral implant 10 of the interbody implant system, described above, can be inserted with intervertebral disc space I to space apart articular joint surfaces, provide support and maximize stabilization of vertebrae V. It is further contemplated that intervertebral implant 10 provides height restoration between vertebral bodies, decompression, restoration of sagittal balance and/or resistance of subsidence into vertebral endplates.

In use, to treat the affected section of vertebrae V, a medical practitioner obtains access to a surgical site including vertebrae V in any appropriate manner, such as through incision and retraction of tissues. It is envisioned that the interbody implant system can be used in any existing surgical method or technique including open surgery, mini-open surgery, minimally invasive surgery and percutaneous surgical implantation, whereby vertebrae V is accessed through a mini-incision, or sleeve that provides a protected passageway to the area. Once access to the surgical site is obtained, the particular surgical procedure is performed for treating the spine disorder. Intervertebral implant 10, described above with regard to FIGS. 1-9, is then employed to augment the surgical treatment, intervertebral implant 10 can be delivered or implanted as a pre-assembled device or can be assembled in situ. Intervertebral implant 10 can be completely or partially revised, removed or replaced in situ. It is contemplated that one or all of the components of the interbody implant system can be delivered to the surgical site via manual manipulation and/or a free hand technique. It is further contemplated that intervertebral implant 10 may be inserted posteriorly, and then manipulated anteriorly and/or lateral and/or medial.

An incision is made in the body of a patient and a cutting instrument (not shown) creates a surgical pathway for implantation of intervertebral implant 10 within the patient body. A guide instrument (not shown) is employed to initially distract vertebrae V1 from vertebrae V2. A sleeve or cannula (not shown) is used to access intervertebral disc space I and facilitate delivery and access for components of the interbody implant system. A preparation instrument (not shown) can be inserted within the sleeve or cannula and disposed within intervertebral disc space I. The preparation instrument(s) can be employed to remove some or all of the disc tissue including the disc nucleus and fluids, adjacent tissues and/or bone, corticate, scrape and/or remove tissue from the surfaces of endplates of opposing vertebrae V1, V2, as well as for aspiration and irrigation of the region according to the requirements of a particular surgical application.

Intervertebral implant 10 is disposed in the first, collapsed configuration, described above and delivered through a surgical pathway along a direct lateral approach into intervertebral disc space I with a delivery instrument (not shown) including a driver. The driver delivers intervertebral implant 10 into the prepared intervertebral disc space I, between vertebrae V1 and vertebrae V2, according to the requirements of a particular surgical application.

Figure 10:
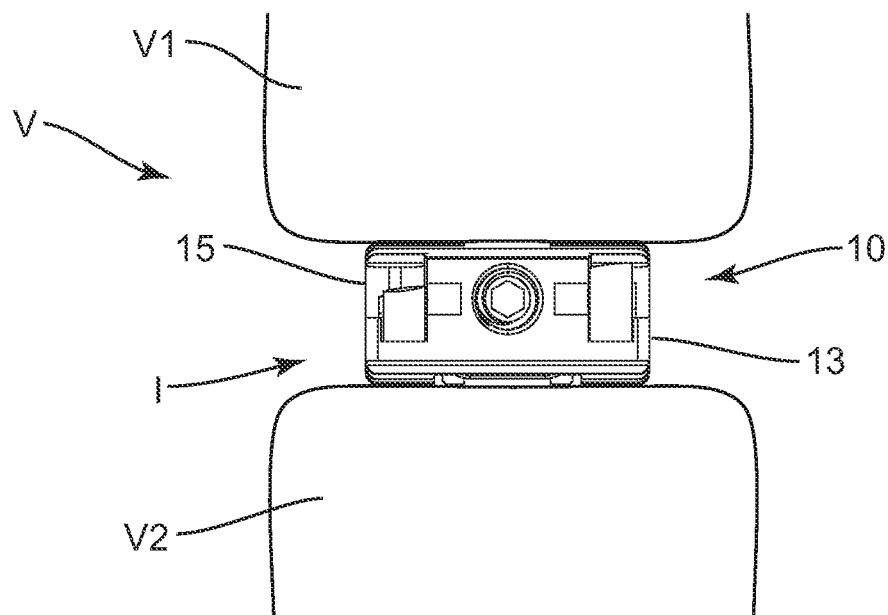
FIG. 10 is a side view of components of a system in accordance with the principles of the present disclosure disposed with vertebrae.
Figure 11:
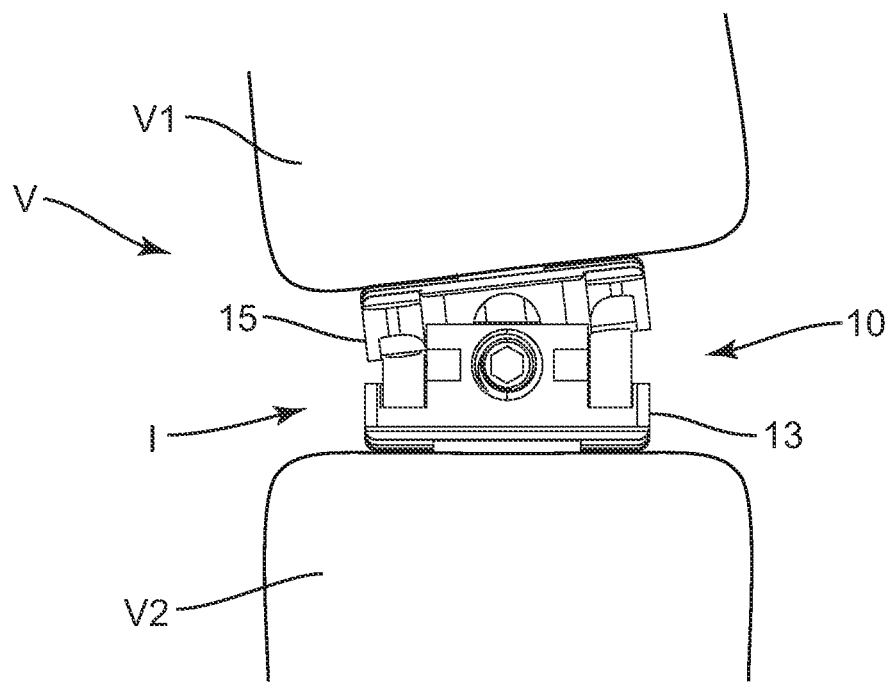
FIG. 11 is a side view of components of the system and vertebrae shown in FIG. 10.

Upon desired positioning of intervertebral implant 10, as shown in FIG. 10, the driver or other instrument engages intervertebral implant 10 to facilitate actuation of the component parts of intervertebral implant 10. The driver engages screw 66 for rotation in a clockwise direction such that screw 66 translates axially to drive wedge 30 axially in the direction shown by arrow A (FIG. 8). Wedge portions 90, 96 slidably engage the respective inclined portions 42, wedge portions 92, 98 slidably engage the respective inclined portions 48 and wedge portions 94, 100 slidably engage the respective inclined portions 53, as shown and described with regard to FIGS. 6-9. Such slidable engagement of the surfaces of wedge 30 and components 16, 18, due to the axial translation of wedge 30, pivots component 16 relative to component 18 in rotation such that components 16, 18 expand between the first collapsed configuration and a second, expanded configuration, as shown in FIG. 11. This configuration facilitates expansion of intervertebral implant 10 such that anterior end 13 has a greater rate and amount of expansion relative to posterior end 15. It is contemplated that in the expanded configuration, intervertebral implant 10 provides height restoration between vertebrae V1 and vertebrae V2, decompression, restoration of sagittal balance and resistance of subsidence into the endplates of vertebrae V1 and vertebrae V2.

It is envisioned that the components of the interbody implant system, which may include one or a plurality of intervertebral implants 10, can be delivered to the surgical site via alternate approaches. In one embodiment, intervertebral implant 10 is delivered through the surgical pathway along a transforaminal lumbar interbody fusion approach into intervertebral disc space I and disposed in the expanded configuration. In one embodiment, a plurality of intervertebral implants 10 are delivered through the surgical pathway along a posterior lumbar interbody fusion approach into intervertebral disc space I and disposed in the expanded configuration in a side by side orientation.

In one embodiment, intervertebral implant 10 can be collapsed from the expanded configuration to an alternate configurations between the expanded and collapsed configurations, as described above, to collapse intervertebral implant 10 as may be desired to reposition with or remove intervertebral implant 10 from intervertebral disc space I. In one embodiment, the interbody implant system includes a plurality of intervertebral implants 10, which can be variously sized and configured, and/or oriented in a side by side engagement, spaced apart and/or staggered.

In one embodiment, the interbody implant system includes an agent, which can include a bone growth promoting material, which may be disposed, packed or layered within, on or about the components and/or surfaces of the interbody implant system. The bone growth promoting material, such as, for example, bone graft can be a particulate material, which may include an osteoconductive material such as HA and/or an osteoinductive agent such as a bone morphogenic protein (BMP) to enhance bony fixation of intervertebral implant 10 with the adjacent vertebrae V.

It is contemplated that the agent and/or bone graft may include therapeutic polynucleotides or polypeptides. It is further contemplated that the agent and/or bone graft may include biocompatible materials, such as, for example, biocompatible metals and/or rigid polymers, such as, titanium elements, metal powders of titanium or titanium compositions, sterile bone materials, such as allograft or xenograft materials, synthetic bone materials such as coral and calcium compositions, such as HA, calcium phosphate and calcium sulfite, biologically active agents, for example, gradual release compositions such as by blending in a bioresorbable polymer that releases the biologically active agent or agents in an appropriate time dependent fashion as the polymer degrades within the patient. Suitable biologically active agents include, for example, BMP, Growth and Differentiation Factors proteins (GDF) and cytokines. Intervertebral implant 10 can be made of radiolucent materials such as polymers. Radiomarkers may be included for identification under x-ray, fluoroscopy, CT or other imaging techniques. It is envisioned that the agent may include one or a plurality of therapeutic agents and/or pharmacological agents for release, including sustained release, to treat, for example, pain, inflammation and degeneration.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. An intervertebral implant comprising:
   a first component comprising an outer tissue engaging surface and an inner surface;
   a second component connected to the first component, and being relatively moveable therefrom, the second component comprising an outer tissue engaging surface and an inner surface, the second component including an actuator, the actuator comprising a screw engaged with the second component; and
   a third component disposed for engagement and being movable relative to the first and second components, the third component comprising a first ramp and a second ramp axially spaced apart from the first ramp, the third component comprising a first rail including at least a portion of each of the first ramp and the second ramp and a second rail including at least a portion of each of the first ramp and the second ramp, at least one of the ramp portions disposed with the first rail has a first height and at least one of the ramp portions disposed with the second rail has a second height, the first height being greater than the second height,
   wherein the actuator is fixedly connected with the third component to effect axial translation of the third component such that the ramps engage the inner surface of one of the first component and the second component to move the components between a first, collapsed configuration and a second, expanded configuration.

2. An intervertebral implant as recited in claim 1, wherein the first rail is disposed relative to the second rail such that the first height and the second height define a lordotic angle in a range of 5 to 30 degrees.

3. An intervertebral implant as recited in claim 1, wherein the third component includes a third ramp axially spaced apart from the second ramp, the first and second rails each including at least a portion of the third ramp.

4. An intervertebral implant as recited in claim 1 wherein the first rail is spaced apart and disposed in a substantially parallel orientation relative to the second rail.

5. An intervertebral implant as recited in claim 1 wherein the first rail is spaced apart and separated from the second rail by an open cavity.

6. An intervertebral implant as recited in claim 1 wherein the first rail is spaced apart and connected to the second rail via a wall disposed therebetween, the wall being configured for connection with the actuator.

7. An intervertebral implant as recited in claim 6 wherein the second component includes a wall that defines a threaded opening configured for engagement with the screw of the actuator.

8. An intervertebral implant as recited in claim 1 wherein at least one of the ramps define an angle of inclination in the range of 5-60 degrees.

9. An intervertebral implant as recited in claim 1 wherein each of the ramps define an angle of inclination in the range of 5-60 degrees.

10. An intervertebral implant as recited in claim 1 wherein the first, second and third components define a bone graft cavity, the bone graft cavity maintaining a substantially constant volume during axial translation.

11. An intervertebral implant as recited in claim 1 wherein the first, second and third components define a bone graft cavity defining an axial length, the axial length decreasing as the first and second components move from the first to the second configuration.

12. An intervertebral implant as recited in claim 1 wherein the first, second and third components define a bone graft cavity, the actuator defining a longitudinal axis such that the actuator is capable of compressing bone graft disposed in the bone graft cavity along the longitudinal axis during axial translation.

13. An intervertebral implant comprising:
   a piston component comprising an endplate surface and an inner surface disposed in an opposing orientation relative to the endplate surface, the piston component extending between an anterior end and a posterior end;
   a base component comprising an endplate surface and an inner surface disposed in an opposing orientation relative to the endplate surface of the base component, the base component extending between an anterior end and a posterior end, the base component including an actuator, the actuator comprising a screw engaged with the base component;
   a wedge disposed for engagement and being movable relative to the piston and base components, the wedge comprising at least a first ramp and a second ramp axially spaced apart from the first ramp, the wedge further comprises an anterior rail including at least a portion of each of the first ramp and the second ramp, and a posterior rail including at least a portion of each of the first ramp and the second ramp, at least one of the ramp portions disposed with the anterior rail has a first height and at least one of the ramp portions disposed with the posterior rail has a second height, the first height being greater than the second height
   wherein the actuator is fixedly engaged with the wedge to effect axial translation of the wedge such that the ramps engage the inner surface of the piston component to move the components between a first, collapsed configuration and a second, expanded configuration.

14. An intervertebral implant as recited in claim 13 wherein the anterior rail is disposed relative to the posterior rail such that the first height and the second height define a lordotic angle in a range of 5 to 30 degrees.

15. An intervertebral implant as recited in claim 13 wherein the anterior rail is spaced apart and separated from the posterior rail by an open cavity.

16. An intervertebral implant as recited in claim 13 wherein each of the ramps define an angle of inclination in the range of 5-60 degrees.

17. An intervertebral implant as recited in claim 13 wherein the piston and base components define a bone graft cavity, the bone graft cavity maintaining a substantially constant volume during axial translation.

18. An intervertebral implant as recited in claim 13 wherein the piston, wedge and base components define a bone graft cavity, the actuator defining a longitudinal axis such that the actuator is capable of compressing bone graft disposed in the bone graft cavity along the longitudinal axis during axial translation.

\* \* \* \* \*